United States Patent
Maeda et al.

(10) Patent No.: US 10,429,373 B2
(45) Date of Patent: Oct. 1, 2019

(54) METHOD FOR DIAGNOSING ROLLING DEVICE

(71) Applicant: NSK LTD., Tokyo (JP)

(72) Inventors: Masayuki Maeda, Fujisawa (JP);
Taisuke Maruyama, Fujisawa (JP);
Ken Nakano, Yokohama (JP)

(73) Assignee: NSK LTD., Tokyo (JP)

( * ) Notice: Subject to any disclaimer, the term of this patent is extended or adjusted under 35 U.S.C. 154(b) by 0 days.

(21) Appl. No.: 16/089,869

(22) PCT Filed: Dec. 13, 2017

(86) PCT No.: PCT/JP2017/044745
§ 371 (c)(1),
(2) Date: Sep. 28, 2018

(87) PCT Pub. No.: WO2018/128062
PCT Pub. Date: Jul. 12, 2018

(65) Prior Publication Data
US 2019/0128866 A1 May 2, 2019

(30) Foreign Application Priority Data

Jan. 6, 2017 (JP) .................. 2017-001019

(51) Int. Cl.
*G01R 27/26* (2006.01)
*G01N 33/28* (2006.01)
*G01N 33/30* (2006.01)
*G01N 27/06* (2006.01)
*G01M 13/04* (2019.01)
*G01N 27/22* (2006.01)

(52) U.S. Cl.
CPC ........ *G01N 33/2888* (2013.01); *G01M 13/04* (2013.01); *G01N 27/221* (2013.01); *G01N 27/06* (2013.01)

(58) Field of Classification Search
CPC .... G01R 27/26; G01N 33/28; G01N 33/2888; G01N 33/30; G01N 27/06; G01N 27/221; G01M 13/04; G01L 3/02; F03D 11/00
See application file for complete search history.

(56) References Cited

U.S. PATENT DOCUMENTS 5,001,435 A    3/1991  Smith
5,927,865 A *  7/1999  Ito .......................... F16C 33/62
                                                      384/492

(Continued)

FOREIGN PATENT DOCUMENTS

JP    63-290936 A   11/1988
JP     4-96617 U    8/1992

(Continued)

OTHER PUBLICATIONS

Schnabel, S. et al., "Monitoring of Running-in of an EHL Contact Using Contact Impedance", Tribology Letters, Jul. 29, 2016, 65:35, pp. 1-10, [retrieved on Feb. 5, 2018], Internet: (https://link.springer.com/article/10.1007/s11249-016-0727-2).

(Continued)

*Primary Examiner* — Neel D Shah
(74) *Attorney, Agent, or Firm* — Sughrue Mion, PLLC

(57) ABSTRACT

A method is for diagnosing a rolling device comprising an outer member, an inner member, and a rolling element. The method includes applying an alternating voltage to an electric circuit configured by the outer member, the rolling element and the inner member, measuring an impedance and a phase of the electric circuit when the alternating voltage is applied to the electric circuit, and calculating a lubrication film thickness and a metallic contact ratio between the outer member and the rolling element and/or between the inner member and the rolling element, based on a measured impedance and a measured phase.

5 Claims, 4 Drawing Sheets

(56) References Cited

U.S. PATENT DOCUMENTS

| | | | | |
|---|---|---|---|---|
| 2002/0083779 | A1* | 7/2002 | Narita | G01M 13/045 73/862.191 |
| 2003/0091255 | A1* | 5/2003 | Sakoda | F16C 19/225 384/565 |
| 2006/0210208 | A1* | 9/2006 | Ota | F16C 19/163 384/527 |
| 2006/0243068 | A1* | 11/2006 | Ueno | F16C 19/184 73/862.322 |
| 2009/0016664 | A1* | 1/2009 | Tsujimoto | F16C 19/364 384/576 |
| 2009/0304318 | A1* | 12/2009 | Konno | F16C 19/52 384/492 |
| 2013/0034439 | A1* | 2/2013 | Bauer | F03D 7/0224 416/1 |

FOREIGN PATENT DOCUMENTS

| | | |
|---|---|---|
| JP | 2002-131187 A | 5/2002 |
| JP | 4942496 B2 | 5/2012 |
| JP | 2012-163101 A | 8/2012 |

OTHER PUBLICATIONS

Search Report dated Feb. 27, 2018 by the International Searching Authority in counterpart International Patent Application No. PCT/JP2017/044745. (PCT/ISA/210).

Written Opinion dated Feb. 27, 2018 by the International Searching Authority in counterpart International Patent Application No. PCT/JP2017/044745. (PCT/ISA/237).

* cited by examiner

ENLARGED VIEW

INPUT ω,V    OUTPUT Z,θ

METHOD FOR DIAGNOSING ROLLING DEVICE

TECHNICAL FIELD

The present invention relates to a method for diagnosing a rolling device.

RELATED ART

A rolling device such as a bearing has been used in wide industrial fields, including automobiles, diverse industry machines, and the like. It is very important to check a lubrication state in the rolling device, from standpoints of securing smooth operations of a machine, lifetime of the rolling device, and the like. By appropriately checking the lubrication state, it is possible to supply a variety of lubricants (oil, grease and the like) and to perform maintenance such as replacement of the rolling device without insufficiency or excess at a appropriate time. However, since it is difficult to directly observe the lubrication state with naked eyes, a method of monitoring vibrations, sounds and oil film states has been suggested as the method for diagnosing a rolling device.

In Patent Document 1, an alternating voltage is applied to a rotary ring of the rolling device in a contactless state, and an oil film state of the bearing is estimated using a measured capacitance. That is, an electrical equivalent circuit is modeled by regarding the oil film as a capacitor, the alternating voltage is applied to the rotary ring of the rolling device in the contactless state, and a capacitance of the oil film is measured. Since the capacitance and an oil film thickness (a lubrication film thickness) have a correlation, the oil film state is estimated from the correlation.

CITATION LIST

Patent Document

Patent Document 1: Japanese Patent No. 4,942,496B

SUMMARY OF THE INVENTION

Problems To Be Solved By the Invention

According to the technology disclosed in Patent Document 1, it is possible to measure the oil film thickness. However, according to this method, it is possible to calculate only the oil film thickness, and it is difficult to perceive the other factors influencing the lubrication state.

The present invention is to provide a method for diagnosing a rolling device with which it is possible to perceive a lubrication state of the rolling device, considering not only a lubrication film thickness but also a metallic contact ratio.

Means for Solving the Problems

The object of the present invention is achieved by the following structure. A method of the present invention is for diagnosing a rolling device comprising an outer member, an inner member, and a rolling element. The method includes applying an alternating voltage to an electric circuit configured by the outer member, the rolling element and the inner member, measuring an impedance and a phase of the electric circuit when the alternating voltage is applied to the electric circuit, and calculating a lubrication film thickness and a metallic contact ratio between the outer member and the rolling element and/or between the inner member and the rolling element, based on a measured impedance and a measured phase.

Effects of the Invention

According to the present invention, it is possible to perceive the lubrication film thickness and the metallic contact ratio in the rolling device, and to diagnose the lubrication state of the rolling device more specifically and more correctly.

BRIEF DESCRIPTION OF THE DRAWINGS

FIGS. 1A and 1B are conceptual views depicting a contact region between an outer ring or inner ring and a rolling element, in which FIG. 1A depicts a model showing a structure of the contact region and FIG. 1B depicts an electric circuit (equivalent circuit) corresponding to the model of FIG. 1A.

DETAILED DESCRIPTION OF EMBODIMENTS

Hereinafter, an embodiment of a method for diagnosing a rolling device of the present invention will be described in detail with reference to the drawings.

Figure 1A:
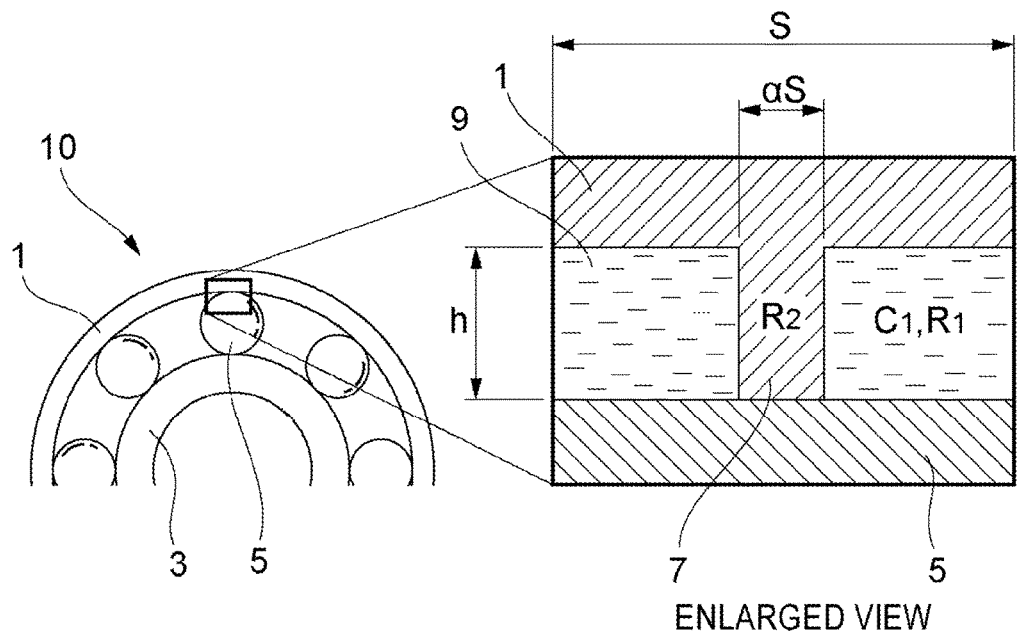
Figure 1B:
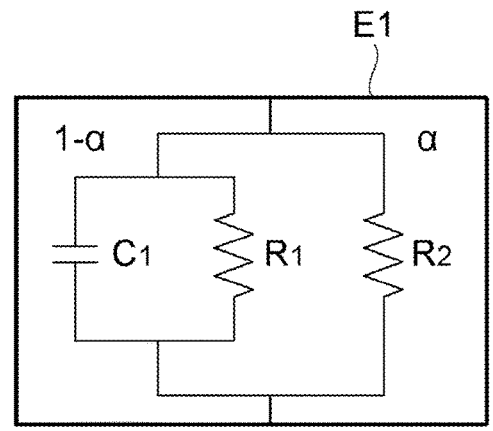

FIGS. 1A and 1B are conceptual views depicting a bearing device as a rolling device, which is a diagnosis target. A bearing device 10 includes a fixed outer ring (outer member) 1, an inner ring (inner member) 3 which is a rotary ring to be fitted to a rotary shaft (not shown), and a plurality of rolling elements 5 interposed between a raceway formed on an inner peripheral surface of the outer ring 1 and a raceway formed on an outer peripheral surface of the inner ring 3. Also, oil films (lubrication film) 9 formed of lubricant such as oil, grease and the like supplied for lubrication are provided between the outer ring 1 and the rolling elements 5 and between the inner ring 3 and the rolling elements 5. The bearing device 10 is applied to a moving body such as an automobile, a two-wheeled vehicle, a train vehicle and the like, an industrial machine, a working machine, and the like. However, the apparatus to be applied is not particularly limited. Also, in FIGS. 1A and 1B, the bearing device 10 of a so-called inner ring rotation type where the rotary shaft is provided to the inner ring-side is shown. However, the present invention is not limited thereto, and can also be applied to a bearing device of a so-called outer ring rotation type where the rotary shaft is provided to the outer ring-side.

The inventors examined a model in which a structure of a contact region as shown in FIG. 1A is modeled with respect to the contact region between the outer ring 1 and the rolling element 5 or between the inner ring 3 and the rolling element 5. That is, in the contact region, there are a part at which each member of the outer ring 1, the inner ring 3, the rolling element 5 and the like is covered with an oil film (lubricant) and a metallic contact part at which metals configuring the respective members of the outer ring 1, the inner ring 3, the rolling element 5 and the like are contacted each other. Therefore, an entire area of the contact region of a specific range is assumed as 5, and a ratio of an area, which is covered by the oil film, of the contact region of the metal part and an area in which metals are contacted each other is assumed as 1-α:α. At this time, an area of a metallic contact part 7 at which metals are contacted each other is αS. A reference numeral h indicates a lubrication film thickness (oil film thickness), which is a thickness of an oil film 9.

Here, as shown in an enlarged view of the contact region between the outer ring 1 and the rolling element 5 (refer to FIG. 1A), when the oil film 9 is regarded as a dielectric body and the outer ring 1 and the rolling element 5 are thought as electrodes, the oil film 9 forms a capacitor $C_1$. The oil film 9 has a resistor $R_1$. When current flows through the oil film (lubrication film) 9, the oil film (lubrication film) 9 has a resistor component, so that it functions as a capacitor and a resistor.

In the meantime, the metallic contact part 7 at which metals are contacted each other has a resistor $R_2$. As a result, as shown in FIG. 1B, an electric circuit (equivalent circuit) E1 (a circuit formed by the outer ring 1 or inner ring 3 and the rolling element 5) corresponding to the model of FIG. 1A is derived. The oil film 9 forms a parallel circuit of the capacitor $C_1$ (capacitance $C_1$) and the resistor $R_1$ (resistance $R_1$), and the parallel circuit and a resistor $R_2$ (resistance $R_2$) formed by the metallic contact part 7 are connected in parallel. As described later, the present invention can diagnose a lubrication state of the rolling device by using the electric circuit to calculate a lubrication film thickness and the metallic contact ratio α, which is a ratio of an occupying area of the metallic contact part 7 to the entire area of the contact region.

Figure 2:
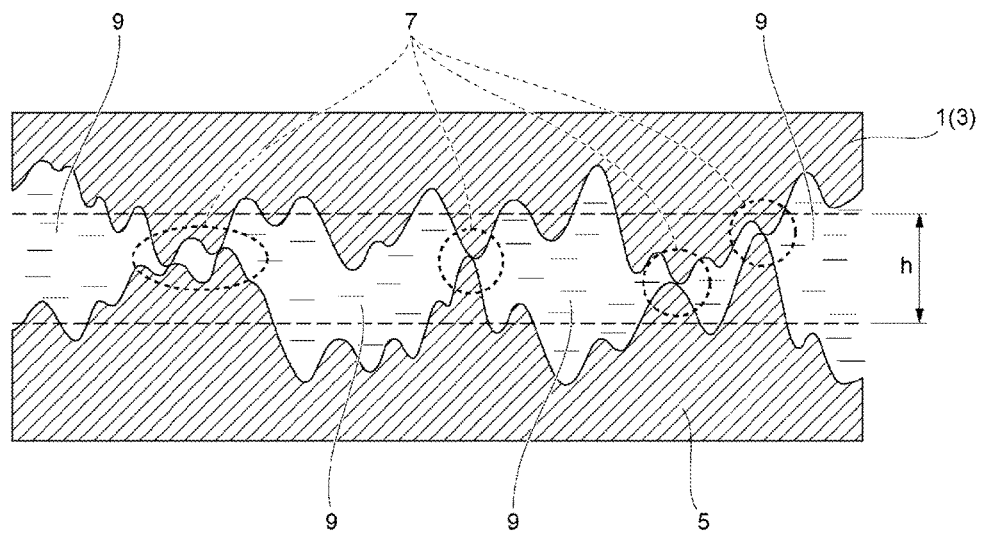
FIG. 2 is a conceptual view depicting unevenness of a surface of the contact region between the outer ring or inner ring and the rolling element.

FIG. 2 is an enlarged view of the contact region between the outer ring 1 or inner ring 3 and the rolling element 5. The surfaces of the outer ring 1, the inner ring 3 and the rolling element 5 are smoothly grinded. However, as shown in FIG. 2, the surfaces have fine unevenness, as seen in a micro manner. The oil film 9 is formed in a space formed by the unevenness. Also, as shown with the broken line, the metallic contact part 7 is formed by a part at which the outer ring 1 or inner ring 3 and the rolling element 5 are directly contacted to each other. Also, the lubrication film thickness h is obtained from an average thickness of the oil film 9 in the contact region of a predetermined range.

Figure 3:
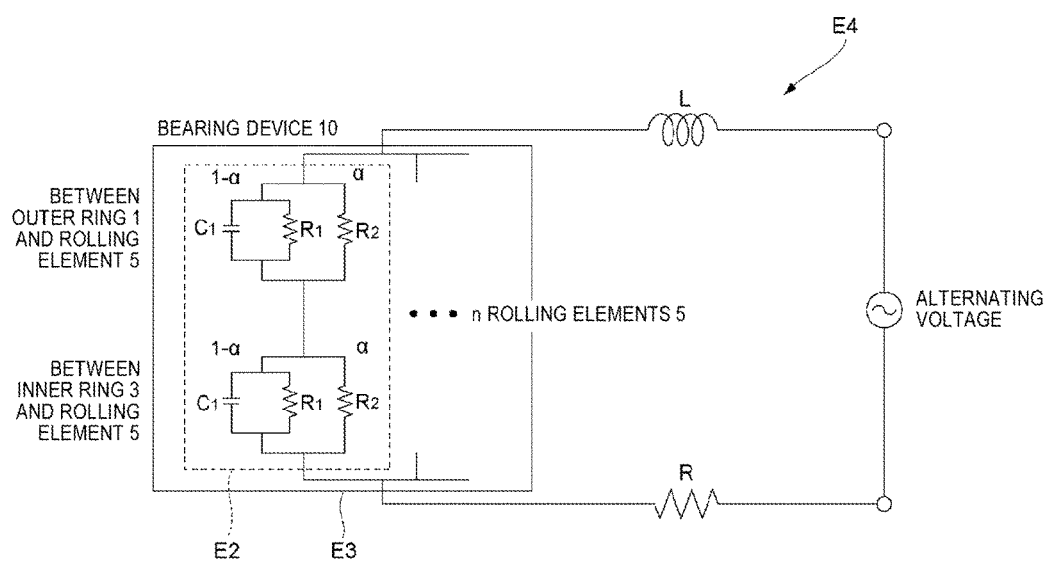
FIG. 3 depicts an electric circuit (equivalent circuit) for diagnosing a bearing device.

FIG. 3 depicts an electric circuit (equivalent circuit) of an embodiment for diagnosing the bearing device 10. As described above, the electric circuit (equivalent circuit) E1 as shown in FIG. 1B is formed between the outer ring 1 or inner ring 3 and each rolling element 5. Since each rolling element 5 is in contact with both the outer ring 1 and the inner ring 3, an electric circuit (equivalent circuit) E2 where the two electric circuits E1 (between the outer ring 1 and the rolling element 5 and between the inner ring 3 and the rolling element 5) are connected in series is formed for each rolling element 5, as shown in FIG. 3.

Also, when the bearing device 10 has the n rolling elements 5, the n electric circuits E2 are connected in parallel. Therefore, as shown in FIG. 3, the bearing device 10 having the n rolling elements 5 forms an electric circuit (equivalent circuit) E3. When diagnosing the bearing device 10 of the embodiment, an alternating voltage is applied from a power supply to between the outer ring 1 and the inner ring 3 of the bearing device 10 in a state where an inductance L of a coil and a resistor R are connected in series with the bearing device 10. Therefore, an entire electric circuit (equivalent circuit) E4 shown in FIG. 3 is formed. In this case, the connection of the inductance L of the coil and the resistor R is just exemplary, and the electric circuit (equivalent circuit) E4 is not necessarily required to be adopted.

A frequency of the alternating voltage is preferably 1 Hz or higher and lower than 1 GHz. When the frequency is lower than 1 Hz or equal to or higher than 1 GHz, information (noise) other than the contact region is much included in an impedance and a phase (which will be described later) to be measured, so that the information in the contact region may not be correctly obtained. Also, a voltage of the alternating voltage is preferably 1 μV or higher and lower than 100 V. When the voltage is lower than 1 μV, the current does not flow through the bearing device 10, so that it is not possible to perform the monitoring. Also, when the voltage is equal to or higher than 100 V, electrical pitting may be caused in the bearing device 10.

In the below, the specific method is described. In the embodiment, as shown in FIG. 3, the diagnosis method of the bearing device 10 includes applying the alternating voltage to the bearing device 10 and obtaining the lubrication film thickness h and the metallic contact ratio α, thereby diagnosing a state of the bearing device 10. When the electric circuit E4 of FIG. 3 is used, the lubrication film thickness h and the metallic contact ratio α are derived by following equations (1) and (2).

[equation 1]

$$h = \omega \varepsilon_1 S \left[ -\frac{n}{2} \left\{ \frac{(Z \sin \theta - \omega L)^2 + (Z \cos \theta - R)^2}{Z \sin \theta - \omega L} \right\} + R_{30} \left( \frac{Z \cos \theta - R}{Z \sin \theta - \omega L} - \frac{Z \cos \theta_1 - R}{Z \sin \theta_1 - \omega L} \right) \right] \quad (1)$$

$$\alpha = \frac{2}{n} \frac{R_{30}}{(Z \sin \theta - \omega L)^2 + (Z \cos \theta - R)^2} \left\{ (Z \cos \theta - R) - \frac{(Z \cos \theta_1 - R)(Z \sin \theta - \omega L)}{Z \sin \theta_1 - \omega L} \right\} \quad (2)$$

The respective symbols have following meanings.
ω: frequency of alternating voltage
$\varepsilon_1$: dielectric constant of lubricant
S: average value of areas of respective contact ellipses when each contact region is approximated to a contact ellipse
n: the number of the rolling elements 5 of the bearing device 10 (the number of balls)
Z: impedance of the entire electric circuit E4
θ: phase
$R_{20}$: resistor of the metallic contact part 7 in state where the oil film 8 is not completely formed
$\theta_1$: phase in state where the oil film 8 is completely formed (in state where there is no contact region of the metal parts)
L: inductance L connected in series with the bearing device 10
R: resistor R connected in series with the bearing device 10

As described above, the lubrication film thickness h is an average thickness of the oil film 9 in the entire contact region between the outer ring 1 or inner ring 3 and the rolling element 5 of the bearing device 10. The metallic contact ratio α is a ratio of an area of the metallic contact part 7 with respect to the entire contact region.

Figure 4:
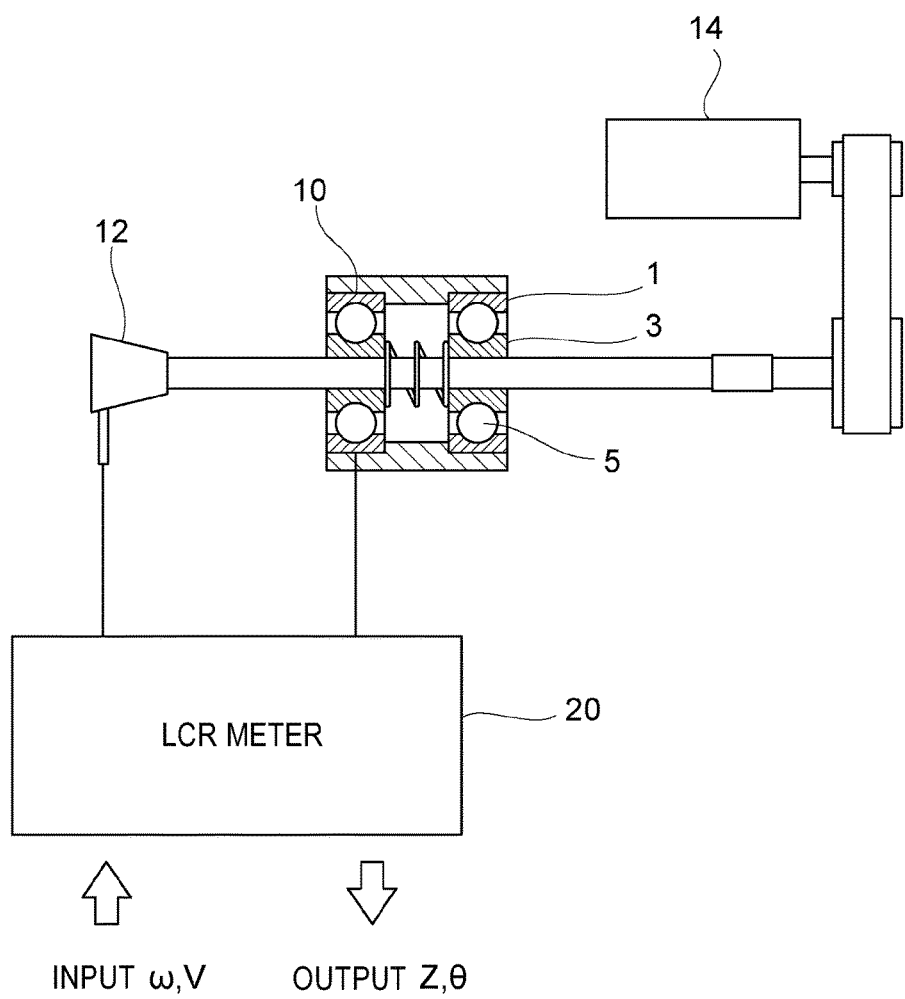
FIG. 4 is a schematic view of a test device.

FIG. 4 is a schematic view of an example of a test device. One end of a drive shaft penetrating the bearing device 10 is connected to a general LCR meter 20 (also serves as the alternating voltage) via a rotary connector 12, and the other end of the drive shaft is connected to a drive motor 14. The rotary connector 12 may be configured by mounting a carbon brush to a rotary ring provided to one end of the drive shaft or mounting a slip ring to the drive shaft. However, the present invention is not limited thereto.

Figure 5:
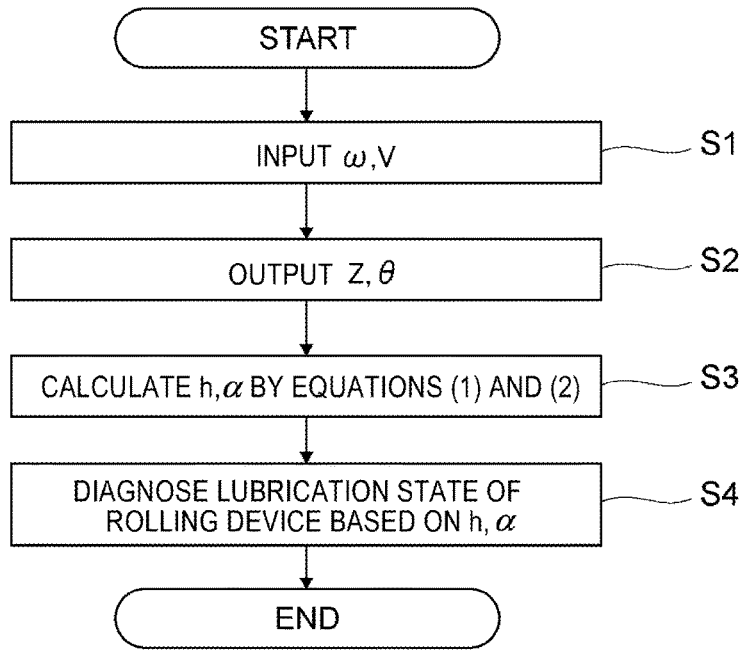
FIG. 5 is a flowchart depicting diagnosis processes of the bearing device.

The state diagnosis of the bearing device 10 is performed using the lubrication film thickness h and the metallic contact ratio α obtained from the equations (1) and (2). FIG. 5 is a flowchart depicting processes of a state diagnosis method of the bearing device 10 using the test device of FIG. 4. First, an operator inputs a frequency ω of the alternating voltage and a voltage V of the alternating voltage to the LCR meter 20 in a state where the motor 14 is driven to rotate the drive shaft (step S1). Receiving the inputs, the LCR meter 20 outputs an impedance Z and a phase θ (step S2). Receiving the outputs, a computer or the like (not shown) calculates the lubrication film thickness h and the metallic contact ratio α from the equations (1) and (2) (step S3). The output in step S2 and the calculation in step S3 are performed more than once time-serially, for example, every predetermined time (every one second, for example). In addition, the computer or operator diagnoses the bearing device 10 from the lubrication film thickness h and the metallic contact ratio α (step S4).

When the lubrication film thickness h has a sufficient size with respect to the surface roughness of the outer ring 1, the inner ring 3 and the rolling element 5 and the metallic contact part 7 is not formed, the relationships of h>0 and α=0 are satisfied and this is an ideal state for the bearing device 10. However, actually, the lubrication film thickness h and the metallic contact ratio α change over time due to diverse factors such as lubricant, operating conditions, operating time and the like. As the temporal changes of the lubrication film thickness h and the metallic contact ratio α, following cases are considered.

(1) The lubrication film thickness h increases and the metallic contact ratio α decreases.

(2) The lubrication film thickness h decreases and the metallic contact ratio α increases.

(3) The lubrication film thickness h increases and the metallic contact ratio α also increases.

(4) The lubrication film thickness h decreases and the metallic contact ratio α also decreases.

It is thought that the state (1) indicates a process that as the metal contact occurs, the surface roughness of the inner and outer rings decreases (so-called mild running-in).

It is thought that the state (2) indicates a contact process of the rolling element 5 and the outer ring 1 and/or inner ring 3.

It is thought that the state (3) indicates a phenomenon that conductive wear debris generated due to wear are introduced between two surfaces (between the outer ring 1 and the rolling element 5 or between the inner ring 3 and the rolling element 5), so that a gap between the two surfaces increases and the lubrication film thickness (specifically, the gap between the two surfaces) h and the metallic contact ratio α resultantly increase. That is, it is thought that the state (3) indicates a process that the conductive wear debris generated due to the wear are introduced into the contact region.

It is thought that the state (4) indicates that the conductive wear debris generated due to the wear are excluded from between the two surfaces and the lubrication film thickness (specifically, the gap between the two surfaces) h and the metallic contact ratio α resultantly decrease. That is, it is thought that the state (4) indicates a process that the conductive wear debris generated due to the wear are excluded from the contact region.

Like this, in the embodiment, it is premised that the electric circuit is configured by the outer ring 1, which is the outer member, the rolling element 5, and the inner ring 3, which is the inner member, and the alternating voltage is applied to the electric circuit. The LCR meter 20 is configured to measure and output the impedance Z and the phase θ of the electric circuit upon the applying of the alternating voltage. Based on the measured impedance Z and phase θ, the lubrication film thickness h and the metallic contact ratio α between the outer ring 1 and the rolling element 5 and/or between the inner ring 3 and the rolling element 5 are calculated using the computational device such as the computer, for example. By the calculation of the values, it is possible to simply and correctly diagnose the state, particularly, the lubrication state of the bearing device 10, which is the rolling device.

Particularly, in the embodiment, the impedance Z and the phase θ are measured more than once time-serially, so that the lubrication film thickness h and the metallic contact ratio α are measured more than once time-serially. As a result, as described in the above (1) to (4), it is possible to perceive the temporal changes of the lubrication film thickness h and the metallic contact ratio α and to diagnose the lubrication state of the rolling device from the temporal changes.

In the below, a specific example is described. The lubrication film thickness h and the metallic contact ratio α were measured using a single-row deep groove ball bearing (model No. 608) having an inner diameter of 8 mm, an outer diameter of 22 mm and a height of 7 mm in which PAO (17 mm$^2$/s, 40° C.), which was poly-α-olefin as the lubricant, was enclosed. The test conditions were the axial load of 19.6 N, the revolution of 500 rpm, the temperature of room temperature and the lubricant-enclosed amount of 0.04g, and the measurement was performed using the test device shown in FIG. 4.

Figure 6:
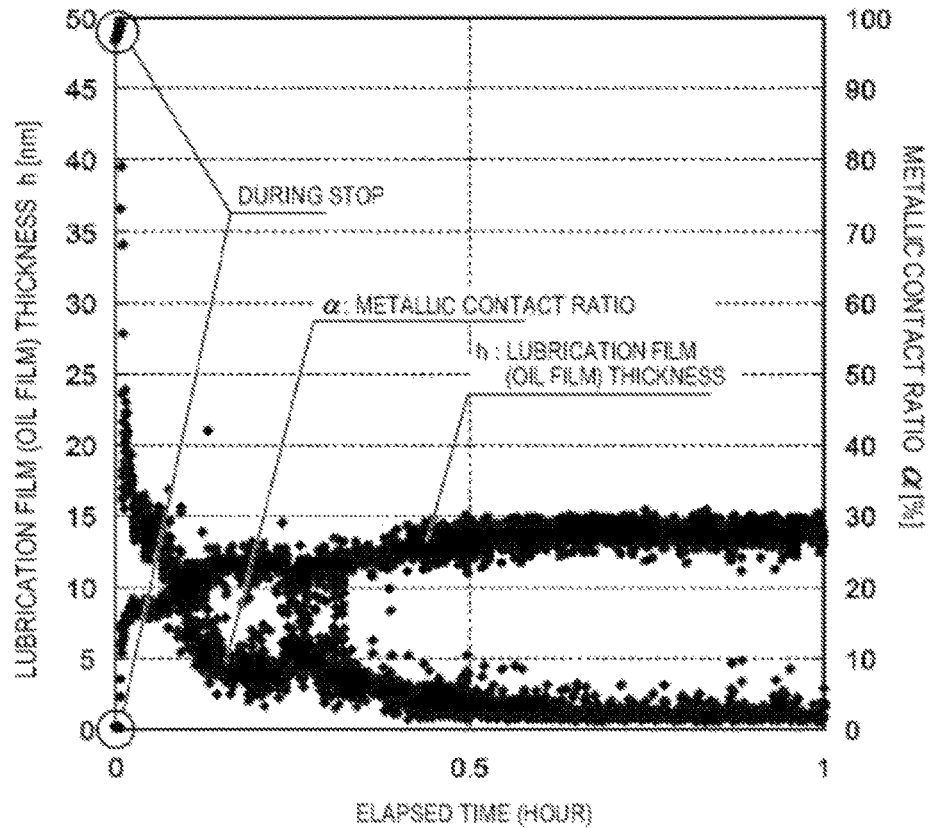
FIG. 6 is a graph depicting temporal changes of a lubrication film thickness and a metallic contact ratio of an embodiment.

FIG. 6 is a graph depicting the temporal changes of the lubrication film thickness h and the metallic contact ratio α up to one hour after the rotation started from a stationary state. According to the test conditions, since the surface roughness was greater than the lubrication film thickness h, the metal contact occurred immediately after the rotation test started. From FIG. 6, it can be seen that before the test (stationary state), the lubrication film thickness was 0 nm and the metallic contact ratio was 100% and after the rotation started, the lubrication film thickness h increased and the metallic contact ratio α decreased. The reason is that the surface roughness of the inner and outer rings decreased (mild conformability) due to the meal contact. In the meantime, the respective values of the example are as follows. $Z_{before}$ is the impedance of the entire electric circuit E4 upon the stop of the bearing, and $\cos \theta_{before}$ is a cosine component of the phase upon the stop of the bearing.

V: 1.0V
ω: 1MHz
$\varepsilon_1$: 1.98
n: 7
$R_{20} = (n/2)(Z_{before} \times \cos \theta_{before} - R)$
$Z_{before}$: 43.4Ω
$\cos \theta_{before} \approx 0.99$
$\theta_1$: −89°
L: 0
R: 0
S: $2.92577 \times 10^{-8} m^2$ In the meantime, the present invention is not limited to the embodiment and can be appropriately modified and improved. In addition, the materials, shapes, sizes, numerical values, forms, number, arrangement places and the like of the respective constitutional elements of the embodiment are arbitrary and are not particularly limited inasmuch as the present invention can be implemented.

The subject application is based on Japanese Patent Application No. 2017-001019 filed on Jan. 6, 2017, the contents of which are incorporated herein by reference.

DESCRIPTION OF REFERENCE NUMERALS

1: outer ring (outer member)
3: inner ring (inner member)
5: rolling element
7: metallic contact part
9: oil film (lubrication film)
10: bearing device (rolling device)
12: rotary connector
14: motor
20: LCR meter

The invention claimed is:

1. A method for diagnosing a rolling device comprising an outer member, an inner member, and a rolling element, the method comprising:
providing a lubrication film between the outer member and the rolling element and/or between the inner member and the rolling element, wherein when the outer member and the rolling element contact each other and/or the inner member and the rolling element contact each other at a metallic contact part, the metallic contact part forms a resistor $R_2$ in an electric circuit formed between the outer member and the rolling element, and/or between the rolling element and the inner member, the lubrication film and the metallic contact part being connected in parallel in the electric circuit;
applying an alternating voltage to the electric circuit;
measuring an impedance and a phase of the electric circuit when the alternating voltage is applied to the electric circuit, and
calculating a lubrication film thickness between the outer member and the rolling element and/or between the inner member and the rolling element, based on a measured impedance and a measured phase, and
calculating a metallic contact ratio between the outer member and the rolling element and/or between the inner member and the rolling element, based on the measured impedance and the measured phase.

2. The method for diagnosing a rolling device according to claim 1,
wherein the impedance and the phase of the electric circuit are measured time-serially and the lubrication film thickness and the metallic contact ratio are calculated time-serially, and
wherein a lubrication state of the rolling device is diagnosed based on temporal changes of the lubrication film thickness and the metallic contact ratio.

3. The method for diagnosing a rolling device according to claim 1,
wherein a frequency of the alternating voltage is 1 Hz or higher and lower than 1 GHz.

4. The method for diagnosing a rolling device according to claim 1,
wherein the alternating voltage is 1 µV or higher and lower than 100 V.

5. The method for diagnosing a rolling device according to claim 1, wherein the lubrication film forms a parallel circuit of a capacitor $C_1$ and a resistor $R_1$.

* * * * *